United States Patent [19]
Haber et al.

[11] Patent Number: 5,445,614
[45] Date of Patent: Aug. 29, 1995

[54] PHARMACEUTICAL STORAGE AND MIXING SYRINGE

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 140,287

[22] Filed: Oct. 20, 1993

[51] Int. Cl.[6] ............................................. A61M 37/00
[52] U.S. Cl. .................................. 604/89; 604/91; 604/191
[58] Field of Search .................. 604/56, 82, 83, 85, 604/89, 91, 191, 218, 236, 238, 249; 222/135, 137, 387

[56] References Cited

U.S. PATENT DOCUMENTS

| | | |
|---|---|---|
| 4,381,778 | 5/1983 | Kozam et al. ............ 604/191 |
| 4,609,371 | 9/1986 | Pizzino ................... 604/249 |
| 4,620,794 | 11/1986 | Leka ..................... 222/137 |
| 4,689,042 | 8/1987 | Sarnoff et al. ........... 604/89 |
| 5,067,948 | 11/1991 | Haber et al. . |
| 5,114,411 | 5/1992 | Haber et al. . |
| 5,147,323 | 9/1992 | Haber et al. . |
| 5,211,285 | 5/1993 | Haber et al. . |
| 5,240,146 | 8/1993 | Smedley et al. . |
| 5,281,198 | 1/1994 | Haber et al. . |
| 5,290,259 | 3/1994 | Fischer ................... 604/218 |

Primary Examiner—C. Fred Rosenbaum
Assistant Examiner—V. Alexander
Attorney, Agent, or Firm—Townsend and Townsend Khourie and Crew

[57] ABSTRACT

A unitary syringe assembly including a diluent syringe and a jell syringe stores and enables convenient transport of isolated components required for injection. A valve is placed between the two syringes. Immediately before required injection, the valve is opened and intermixing injection and reception of the diluent and jell between the two syringes occurs to thoroughly intermix the diluent and jell. The valve aperture size is selected to provide viscous resistance by the jell until thorough mixing has occurred to provide the user with a tactile indication of sufficient mixing. Upon complete mixing, a needle is attached and injection occurs. Paired side-by-side unitary syringes are utilized with an interconnecting mixing manifold with injection occurring from one syringe only to enable higher needle injection pressure.

11 Claims, 3 Drawing Sheets

PHARMACEUTICAL STORAGE AND MIXING SYRINGE

This invention relates to syringes. More particularly, a syringe construction is shown in which isolated transport of a jell and a diluent in separate measured and isolated quantities occurs to avoid the otherwise short shelf life of the jell/diluent mixture. The separate cylinders fastened together as a unitary assembly are interconnected by a valve which enables mixing of the jell and diluent immediately before injection. The resultant short shelf life of the diluent/jell mixture does not require handling either outside of the syringes or manipulation of separate syringes relative to a special mixing appliance.

BACKGROUND OF THE INVENTION

Certain pharmaceuticals for injection must be stored and transported in a jell format. Unfortunately, these pharmaceuticals in the jell format are too viscous for direct injection. Some of these jells are utilized in chemotherapy.

A preferred jell here used would comprise a cytotoxant and a bulking agent. A preferred low viscosity diluent would comprise a vaso-constricting agent. The jell or high viscosity factor contains a cytotoxin mixed with a biocompatible bulking agent. The diluent or lower viscosity factor comprises a vaso-constrictor to inhibit blood supply to the tumor.

Presence of the bulking agent structures stabilizes the location of the implant within the tumor so as to retain the most effective positioning for the most protracted time period possible. Unfortunately, this effect is of short duration. Thus mixing is required immediately prior to injection. By way of example, a common injected dosage included 9 cc of jell with 0.9 cc of diluent.

The present solution to this problem is to package, store and ship the diluent in one syringe and the jell in another syringe. Immediately before injection, the two separate syringes are opened and connected to a mixing manifold. Thereafter, injection to and from each syringe occurs. Finally, when mixture has occurred, substantially all of the mixed jell and diluent is injected to one syringe—for example the syringe that originally transported the jell. Thereafter, injection conventionally occurs.

The manipulation of two separate glass syringes to a separate fitting immediately prior to injection is burdensome and unduly complex for the modern medical environment. What is needed is a unitary assembly which is self contained and user friendly to the required mixing.

SUMMARY OF THE INVENTION

A unitary syringe assembly including a diluent syringe and a jell syringe stores and enables convenient transport, of isolated components required for injection. A valve is placed between the two syringes. Immediately before required injection, the valve is opened and intermixing injection and reception of the diluent and jell between the two syringes occurs to thoroughly intermix the diluent and jell. The valve aperture size is selected to provide viscous resistance by the jell until thorough mixing has occurred to provide the user with a tactile indication of sufficient mixing. Upon complete mixing, a needle is attached and injection occurs. Paired side-by-side unitary syringes are utilized with an interconnecting mixing manifold with injection occurring from one syringe only to enable higher needle injection pressure.

DESCRIPTION OF THE PREFERRED EMBODIMENT

In the following description, an outline will be followed. The main elements of the invention will first be summarily identified. Thereafter, a detailed description of each of these elements will be made—with major reference to the exploded view provided herewith. Finally, operation will be set forth. This operation will be discussed first with respect to the loading for transport and storage of the syringes here shown and secondly with use of the syringe assembly for mixture and usual injection.

Figure 1:
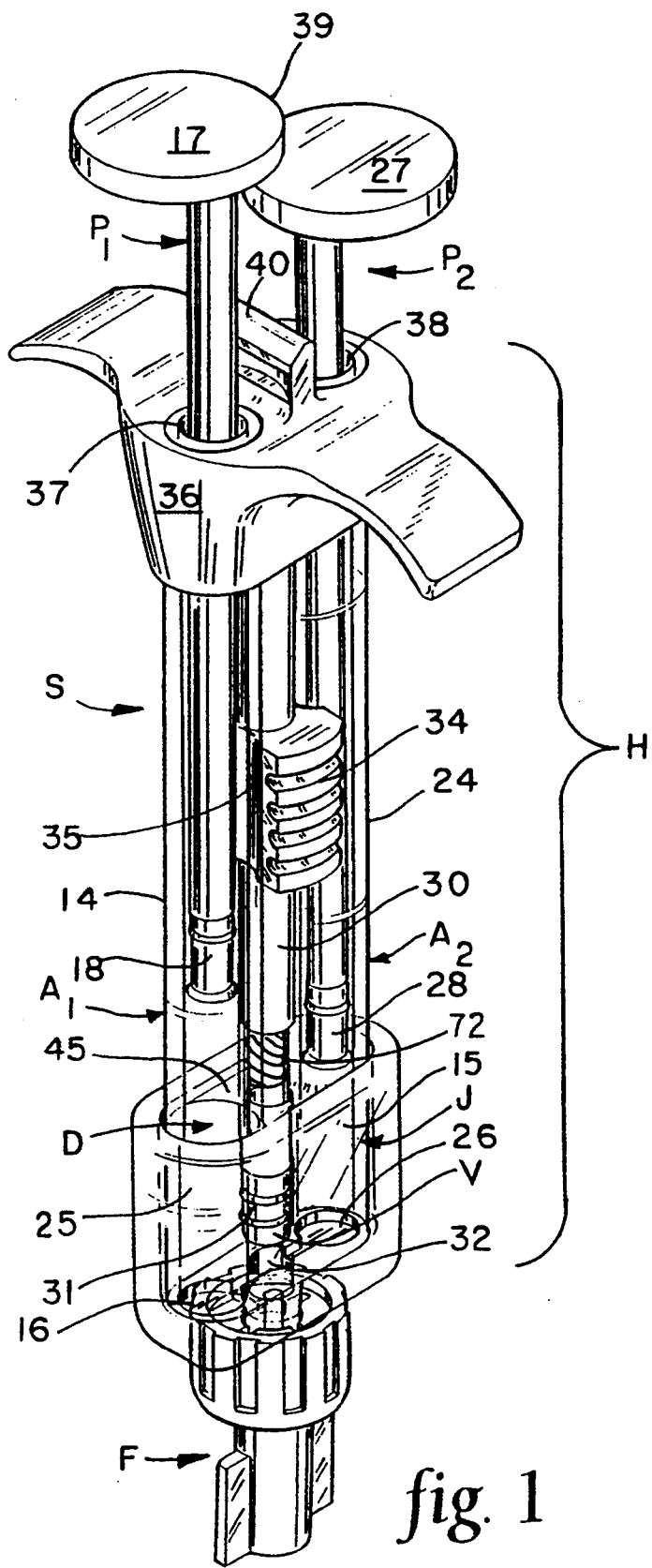
FIG. 1 is a perspective assembled view of a unitary syringe assembly utilizing side by side syringes interconnected at an isolation valve for jell/diluent isolating upon transport and storage and intermixture of the jell-/diluent immediately prior to needle attachment for injection at the illustrated needle fitting.
Figure 3:
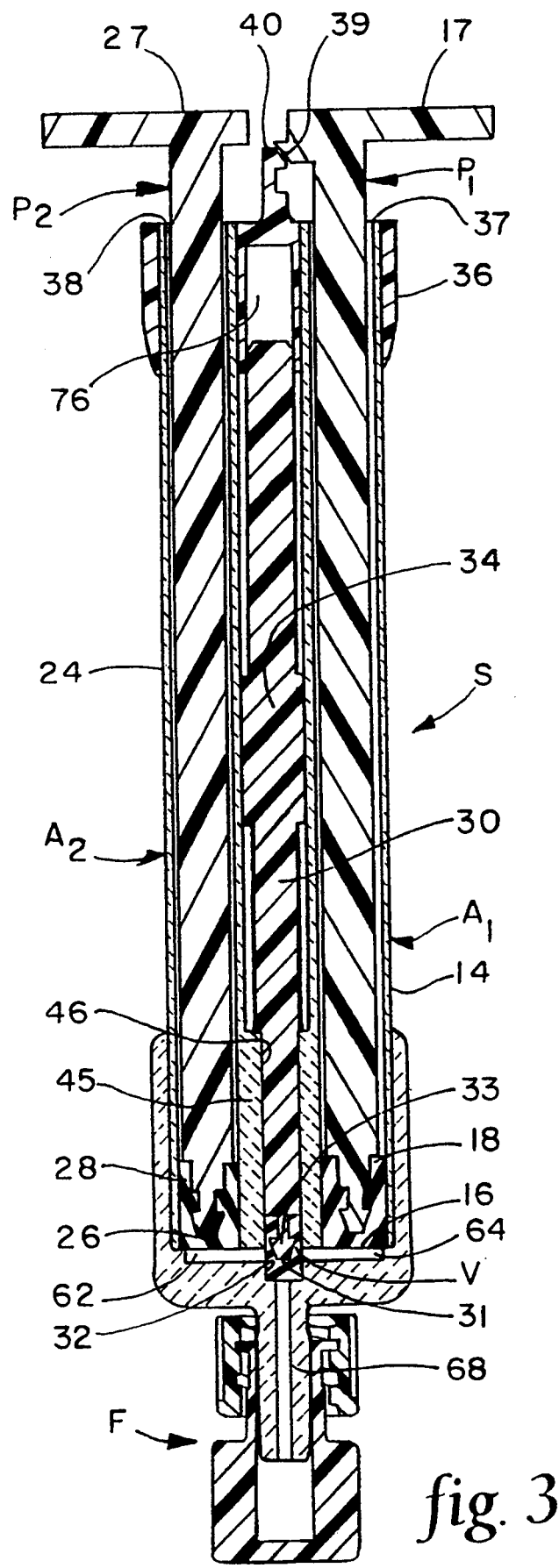
FIG. 3 is a cross section of the embodiment of FIG. 1 illustrating the isolated jell and diluent storage and transport compartments and displaying the isolation valve so that its operation can be understood.

With respect to FIGS. 1 and 3, unitary syringe S of the first embodiment is illustrated. Referring briefly to FIG. 1, first syringe assembly $A_1$ having diluent containing volume D is illustrated. Second syringe assembly $A_2$ having jell containing volume J is shown.

First syringe assembly $A_1$ includes cylinder 14, cylinder outlet 16 and sealing piston 18. Second syringe assembly $A_2$ includes cylinder 24, cylinder outlet 26, and sealing piston 28.

First piston 18 in syringe assembly $A_1$ is displaced by first plunger $P_1$. Second piston 28 in syringe assembly $A_2$ is displaced by plunger $P_2$. It will be more completely understood that the respective syringe assemblies $A_1$, $A_2$ are mounted side-by-side within a common housing H.

Referring to FIG. 1, because the jell 15 and diluent 25 are required to be stored and transported in isolation one from another, it is required that a valve V separate the two substances. Valve V includes a stem 30 fixed between syringe assemblies $A_1$ and $A_2$ with a valve stopper 31 fitting within valve seat 32. As will hereafter be more clearly set forth, once stem 30 moves longitudinally upward, communication through valve V will occur, permitting jell 15 to be mixed with diluent 25.

Finally, there is mounted a fitting F for dispensing the mixed jell 15 and diluent 25. In the case of utilizing syringe S for injection through a needle, fitting F constitutes a standard luer fitting for the attachment of a needle—the needle not being shown. As will here in after be more fully set forth, once stem 30 is moved upward, valve stopper 31 clears seat 32 so mixing can occur. When mixing is complete, plunger $P_1$ is locked in the depressed position, and all mixed diluent and jell are displaced to syringe assembly $A_2$. Thereafter, a conventional needle is affixed to fitting F and the mixed jell and diluent injected.

Figure 2:
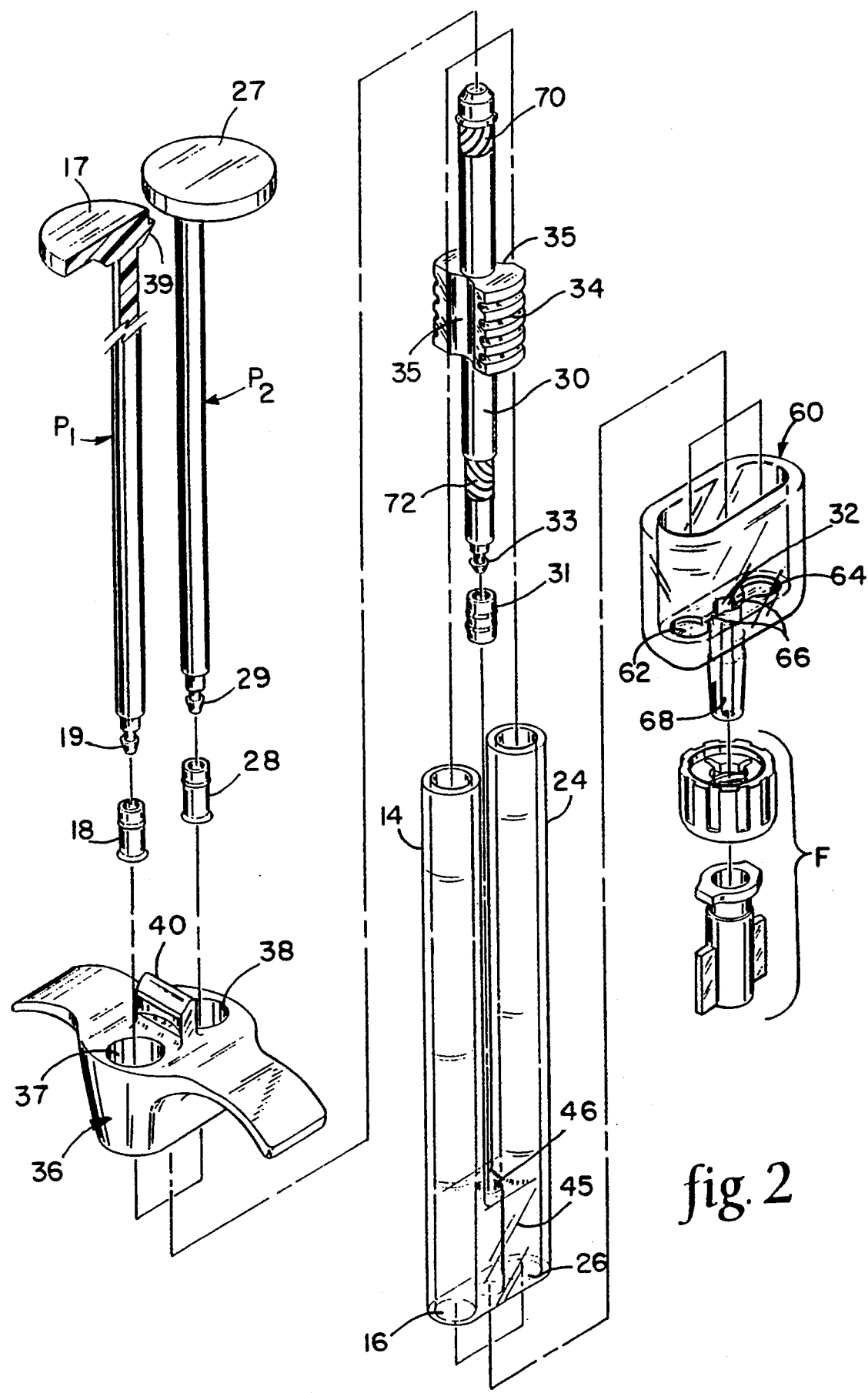
FIG. 2 is a perspective exploded view of the components of the assembled unitary syringe assembly of FIG. 1.

Having set forth the main operative components, the detailed construction of these component will be set forth with primary reference to the exploded view of FIG. 2 and reference when necessary to FIGS. 1 and 3.

Plungers $P_1$ and $P_2$ include finger respective depressing flanges 17, 27 and piston engagers 19, 29 for engaging respective pistons 18, 28.

Top 36 includes respective apertures 37, 38 for respective syringe assemblies $A_1$ and $A_2$. Plungers $P_1$ and $P_2$ fit through these respective apertures. As will hereafter be set forth, piston $P_1$ is provided with a plunger detent 39 which mates with a top detent 40. Such mating is provided upon compression by plunger $P_1$ of stopper 18 to lock plunger $P_1$ with respect to top 36. Thereafter, injection may occur using plunger $P_2$.

Valve V includes seat 32 in bottom 60. Valve stem 30 has valve stopper 31 for engagement to seat 32. Stopper engager 33 joins valve stopper 31 to the bottom of stem 30. Stem 30 is moved by valve handle 34 which rides between cylinders 14, 24 of syringe assemblies $A_1$ and $A_2$.

Cylinders 14, 24 are connected by connector strip 45 at the bottom of the cylinders. Connector strip 45 includes bore 46 which permits both stem 30 and stopper 31 to seat on valve seat 32 in bottom 60.

Bottom 60 includes first syringe exit 62, second syringe exit 64 and interconnecting channels 66. Valve seat 32 connects by interconnecting channels 66 to the respective exits 62, 64. A standard Luer lock fitting F is provided. This fitting remains in the closed position during mixing of the contents of syringe assemblies $A_1$ and $A_2$. When the contents are mixed, syringe assembly $A_1$ at plunger $P_1$ is locked in place and all mixed contents are displaced to syringe assembly $A_2$. Thereafter, injection occurs utilizing syringe assembly $A_2$ and its plunger $P_2$.

Valve stem 30 includes a red band 70 and a green band 72. These respective bands are alternately visible from top 36 at bore 76 and bottom 60 at bore 46. These bands serve to indicate the closed (red) or open (green) alternate states of valve V.

Having described the detailed sections of the exploded view, operation will now be set forth. Loading with the isolated jell and diluent will first be set forth. Thereafter, mixing and injection will be set forth.

Regarding loading, assembly occurs except for plungers $P_1$ and $P_2$ and respective sealing pistons 18, 28. Valve V is moved to the closed position with valve stopper 31 firmly seated in seat 32. All fluid communication is blocked between syringe assembles $A_1$, $A_2$.

Jell 15 and diluent 25 are metered into respective cylinders 24, 14 of respective syringe assemblies $A_2$, $A_1$. Stoppers 28, 18 are "wine corked" into sealing relation with respect to jell J and diluent D. Thereafter plungers $P_1$ and $P_2$ are seated to complete the assembly.

Use can be simply described. When syringe assembly S is received, stem 30 is down seating stopper 31 within valve seat 32. Seat 32 closes off dispenser outlet 68 as well as channels 66 between respective syringe outlet 62 of first syringe assembly $A_1$ and syringe outlets 64 of second syringe assembly $A_2$. In this state, red band 70 is displayed free of bore 76 in top 36.

The user moves stem 30 upward at valve handle 34. Red band 70 is obscured in bore 76 of top 36 and green band 72 appears exposed from bore 46 of connecting strip 45. At the same time, valve stopper 31 clears valve seat 32 and permits channels 66 to communicate first syringe assembly $A_1$ with second syringe assembly $A_2$. Thereafter, by respective alternate depression of respective plungers $P_1$ and $P_2$ mixing can occur. By way of example, with the respective jell and diluent here utilized, about 30 alternate depressions of the respective plungers $P_1$ and $P_2$ may be required for complete mixing.

Channels 66 are sized to give a tactile indication of complete mixing. Specifically, and when mixing first occurs, jell J will only be partly mixed. This being the case, viscous resistance at channels 66 will make the alternate depression of plungers $P_1$ and $P_2$ difficult. Thereafter, and as mixing continues, effort will be much easier as the diluent acts to reduce viscosity considerably. Thus a tactile signal will be imparted when mixing is complete.

Once mixing is complete, plunger $P_1$ will be depressed beyond its full position of penetration. Depressing will continue until piston 18 is partially compressed. Length of plunger $P_1$ is chosen so that plunger detent 39 engages top detent 40. Plunger $P_1$ will be locked in the down position.

With plunger $P_1$ locked, all contents will be displaced to plunger $P_2$. A needle will be attached to fitting F and injection given with plunger $P_2$.

It will be understood that this invention will admit of modification. Further, it will be realized that an apparatus—with and without the loaded medication—has been disclosed. Further, a process is set forth which can include the entire process of loading and utilizing the syringe or alternately just the end user operation of the loaded medical device.

What is claimed is:

1. A unitary syringe assembly for the isolated storage and transport of two substances with intermixed injection of said two substances comprising:

a first syringe assembly for containing a first of said two substances, said syringe assembly including a cylinder, cylinder outlet, and sealing piston for sealing said first substance within said first syringe assembly;

first plunger means for displacing said sealing piston of said first syringe to cause substances in said first syringe to be likewise displaced out said cylinder outlet;

a second syringe assembly for containing a second of said two substances, said syringe assembly including a cylinder, cylinder outlet, and sealing piston for sealing said second substance within said second syringe assembly;

second plunger means for displacing said sealing piston of said second syringe to cause substances in said second syringe to be likewise displaced out said cylinder outlet;

said first and second syringe assemblies being mounted relative to one another in a common housing;

an isolation valve having a housing for permitting communication between said first and second syringes at said cylinder outlets, said isolation valve having first and second relatively moving members, said first and second relatively moving members when in a first relative position preventing communication between said syringes and said first and second members when in a second relative position permitting communication between said syringes;

means for preventing a chosen one of the sealing pistons from moving away from the cylinder outlet when said one of the sealing pistons has been moved to a position near the respective cylinder outlet; and a fitting for mounting of a dispensing head communicated to at least one of said syringes for enabling dispensing of the contents of said communicated syringe through said dispensing head responsive to movement of at least one of said means for displacing.

2. A unitary syringe assembly according to claim 1 and wherein:

said first syringe assembly is mounted side-by-side said second syringe assembly.

3. The unitary syringe assembly of claim 1 wherein the preventing means comprises a first detent on an end of said first plunger means opposite said first sealing piston and a second detent coupled to said first cylinder, said first detent engaging said second detent when said first sealing piston has displaced substantially all of said substances in said cylinder through said cylinder outlet.

4. A unitary syringe assembly loaded with two substances for the isolated storage and transport of said two substances with intermixed injection of said two substances comprising:

first and second substances, one of said substances being a jell and the other of said substances being a diluent for said jell;

a first syringe assembly for containing a first of said two substances, said syringe assembly including a cylinder, cylinder outlet, and sealing piston for sealing said first substance within said first syringe assembly;

one of said two substances loaded in said first syringe assembly between said sealing piston and said cylinder outlet;

means for displacing said sealing piston of said first syringe to cause said substance in said first syringe to be likewise displaced out said cylinder outlet;

a second syringe assembly for containing a second of said two substances, said syringe assembly including a cylinder, cylinder outlet, and sealing piston for sealing said second substance within said second syringe assembly;

the other of said two substances loaded in said second syringe assembly between said sealing piston and said cylinder outlet;

means for displacing said sealing piston of said second syringe to cause substance in said second syringe to be likewise displaced out said cylinder outlet;

said first and second syringe assemblies being mounted relative to one another in a common housing;

an isolation valve having a housing for permitting communication between said first and second syringes at said cylinder outlets, said isolation valve having first and second relatively moving members, said first and second members when in a first relative position preventing communication between said syringes and said first and second members when in a second relative position permitting communication between said syringes; and, a fitting for mounting of a dispensing head communicated to at least one of said syringes for enabling dispensing of the contents of said communicated syringe through said dispensing head responsive to movement of at least one of said means for displacing.

5. A unitary syringe assembly loaded with two substances according to claim 4 and wherein:

said jell comprises a cytotoxant and a bulking agent; and, said diluent would comprise a vaso-constricting agent.

6. A unitary syringe assembly loaded with two substances according to claim 4:

said isolation valve, when said first and second member of said isolation valve are in said second position permitting communication between said members, defines a passage having a dimension to impart a first and stiff resistance to said sealing piston displacing means of said first and second syringe assemblies when said jell and diluent are partially mixed and a second and decreased resistance when said jell and diluent are intermixed whereby an operator of said syringe is given a tactile indication of thorough mixing of said jell and diluent.

7. A method of utilizing a unitary syringe assembly for the isolated storage and transport of two substances with intermixed injection of said two substances comprising:

providing a first syringe assembly for containing a first of said two substances, said syringe assembly including a cylinder, cylinder outlet, and sealing piston for sealing said first substance within said first syringe assembly;

providing means for displacing said sealing piston of said first syringe to cause substances in said first syringe to be likewise displaced out said cylinder outlet;

providing a second syringe assembly for containing a second of said two substances, said syringe assembly including a cylinder, cylinder outlet, and sealing piston for sealing said second substance within said second syringe assembly;

providing means for displacing said sealing piston of said second syringe to cause substances in said second syringe to be likewise displaced out said cylinder outlet;

providing a common housing for said first and second syringe assemblies;

mounting said first and second syringe assemblies relative to one another in said common housing;

providing an isolation valve having a housing for permitting communication between said first and second syringes at said cylinder outlets, said isolation valve having first and second relatively moving members, said first and second members when in a first relative position preventing communication between said syringes and said first and second members when in a second relative position permitting communication between said syringes;

placing said first and second members in said first position preventing communication between said syringe assemblies;

loading said first and second syringe assemblies with said respective first and second substances for transport and storage;

moving said first and second members to said second position whereby said first and second syringe assemblies can communicate one with another;

alternately moving said respective means for displacing said sealing piston of said first and second syringes to cause said substances to move between said first and second syringe assemblies;

providing a fitting for mounting of a dispensing head communicated to at least one of said syringes for enabling dispensing of the contents of said communicated syringe through said dispensing head responsive to movement of at least one of said means for displacing;

sizing said isolation valve so that when said first and second members of said isolation valve are in said second position permitting communication between said members, said isolation valve defines a passage having a dimension to impart a first and stiff resistance to said first and second means for displacing when said substances are partially mixed and a second and decreased resistance when said substances are intermixed whereby an operator of said syringe is given a tactile indication of thorough mixing at said syringes;

mixing said substances until said second and decreased resistance is tactually imparted during said mixing; and, thereafter dispensing said intermixed substances through said dispensing head by moving said at least one of said means for displacing said sealing piston of said syringe assemblies.

8. A method of utilizing a unitary syringe assembly for the isolated storage and transport of two substances with intermixed injection of said two substances, a first substance being a jell and a second substance being a diluent, said unitary syringe assembly having a first syringe assembly containing said first substance, said syringe assembly including a cylinder, cylinder outlet, and sealing piston for sealing said first substance within said first syringe assembly; means for displacing said sealing piston of said first syringe to cause substances in said first syringe to be likewise displaced out said cylinder outlet; a second syringe assembly for containing said second substance, said syringe assembly including a cylinder, cylinder outlet, and sealing piston for sealing said second substance within said second syringe assembly; means for displacing said sealing piston of said second syringe to cause substances in said second syringe to be likewise displaced out said cylinder outlet; a common housing for said first and second syringe assemblies, said first and second syringe assemblies mounted relative to one another in said common housing; and an isolation valve having a housing for permitting communication between said first and second syringes at said cylinder outlets, said isolation valve having first and second relatively moving members, said first and second members when in a first relative position preventing communication between said syringes and said first and second members when in a second relative position permitting communication between said syringes, said first and second members in said first position preventing communication between said syringe assemblies, said first and second syringe assemblies with said respective first and second substances for transport and storage; the method comprising the steps of:

moving said first and second members to said second position whereby said first and second syringe assemblies can communicate one with another;

alternately moving said respective means for displacing said sealing piston of said first and second syringes to cause said substances to move between said first and second syringe assemblies;

providing a fitting for mounting of a dispensing head communicated to at least one of said syringes for enabling dispensing of the contents of said communicated syringe through said dispensing head responsive to movement of at least one of said means for displacing;

sizing said isolation valve so that when said first and second members of said isolation valve are in said second position permitting communication between said members, said isolation valve defines a passage having a dimension to impart a first and stiff resistance to said first and second means for displacing when said jell and said diluent are partially mixed and a second and decreased resistance when said jell and said diluent are intermixed whereby an operator of said syringe is given a tactile indication of thorough mixing at said syringes;

mixing said jell and said diluent until said second and decreased resistance is tactually imparted during said mixing to form an intermixed jell and diluent; and, thereafter dispensing said intermixed jell and diluent through said dispensing head by moving said at least one of said means for displacing said sealing piston of said syringe assemblies.

9. A unitary syringe assembly for the isolated storage and transport of two substances with intermixed injection of said two substances comprising:

a first syringe assembly for containing a first of said two substances, said syringe assembly including a cylinder, cylinder outlet, and sealing piston for sealing said first substance within said first syringe assembly;

first plunger means for displacing said sealing piston of said first syringe to cause substances in said first syringe to be likewise displaced out said cylinder outlet;

a second syringe assembly, mounted side-by-side with said first syringe assembly, for containing a second of said two substances, said syringe assembly including a cylinder, cylinder outlet, and sealing piston for sealing said second substance within said second syringe assembly;

second plunger means for displacing-said sealing piston of said second syringe to cause substances in said second syringe to be likewise displaced out said cylinder outlet;

said first and second syringe assemblies being mounted relative to one another in a common housing;

an isolation valve having a housing for permitting communication between said first and second syringes at said cylinder outlets, said isolation valve having first and second relatively moving members, said first and second relatively moving members when in a first relative position preventing communication between said syringes and said first and second members when in a second relative position permitting communication between said syringes;

said isolation valve comprising a stem independently moveable between said first and second syringes, said stem in a first position preventing communication between said syringe assemblies and in a second position permitting communication between said syringe assemblies;

means for preventing a chosen one of the sealing pistons from moving away from the cylinder outlet; and a fitting for mounting of a dispensing head communicated to at least one of said syringes for enabling dispensing of the contents of said communicated syringe through said dispensing head responsive to movement of at least one of said means for displacing.

10. The unitary syringe assembly of claim 9 and wherein:

said stem includes color coding for displacing at least one color upon movement of said stem to the communication position between said syringe assemblies.

11. The unitary syringe assembly of claim 9 and wherein:

said stem includes color coding for displaying at least one color upon movement of said stem to the isolation position between said syringe assemblies.

* * * * *